US007691805B2

(12) United States Patent
Grubb et al.

(10) Patent No.: US 7,691,805 B2
(45) Date of Patent: Apr. 6, 2010

(54) ANTIMICROBIAL COMPOUNDS

(75) Inventors: Anders Grubb, Lund (SE); Aftab Jasir, Lund (SE); Claes Schalén, Lund (SE); Franciszek Kasprzykowski, Pruszcz Gdanski (PL); Regina Kasprzykowska, Pruszcz Gdanski (PL)

(73) Assignee: Neobiotics AB, Lund (SE)

( * ) Notice: Subject to any disclaimer, the term of this patent is extended or adjusted under 35 U.S.C. 154(b) by 0 days.

(21) Appl. No.: 11/271,109

(22) Filed: Nov. 10, 2005

(65) Prior Publication Data

US 2006/0116327 A1 Jun. 1, 2006

Related U.S. Application Data

(60) Provisional application No. 60/626,490, filed on Nov. 10, 2004.

(30) Foreign Application Priority Data

Nov. 10, 2004 (SE) .................................. 0402734

(51) Int. Cl.
*A61K 38/00* (2006.01)
(52) U.S. Cl. ........................................................ 514/2
(58) Field of Classification Search .................. None
See application file for complete search history.

(56) References Cited

OTHER PUBLICATIONS

Jasir, A. et al., "New Antimicrobia Cystatin C-Based Peptide Active Against Gram-Positive Bacterial Pathogens, Including Methicillin-Resistant Staphyloccus aureus and Multiresistant Coagulase-Negative Staphylocci", Nov. 2003, APMIS, 111:1004-1010.*
Kasprzykowski, F. et al., "Synthesis and Antibacterial Properties of Peptidyl Derivatives and Cyclopeptides Structurally Based Upon The Inhibitory Centre of Human Cystatin C", 2000, APMIS, 108:473-481.*
Abbott, http://www.nature.com/nature/focus/sars/sars3.html.*
Mayo Clinic, http://www.mayoclinic.com/health/polio/DS00572/DSECTION=8.*
Mayo Clinic, http://www.mayoclinic.com/health/hepatitis-a/DS00397/DSECTION=7.*
Mayo Clinic, http://www.mayoclinic.com/health/bird-flu/DS00566/DSECTION=7.*
Jasier et al. "New antimicrobial cystatin C-based peptide active against gram-positive bacterial pathogens, including methicillin-resistant *Staphylococcus aureus* and multiresistant coagulase-negative staphylococci." *APMIS* 2003 vol. III pp. 1004-1010.
Kasprzykowski et al. "Synthesis and antibacterial properties of peptidyl derivatives and cyclopeptides structurally based upon the inhibitory centre of human cystatin C." *APMIS* 2000 vol. 108 pp. 473-481.
Kaspryzykowski et al. "New antimicrobial peptide active against Gram-positive pathogens." *Indian J. Med. Res.* 2004 vol. 119. pp. 74-76.
Panlilio et al. "Methicillin-Resistant Staphylococcus Aureus in U.S. Hospitals, 1975-1991." *Infection Control and Hospital Epidemiology.* vol. 13. No. 10. 1982. pp. 582-586.
Author Unknown. "IUPAC-IUB Joint Commision on Biochemical Nomenclature (JCBN): Nomenclature and Symbolism for Amino Acids and Peptides." *Eur. J. Biochem.* vol. 138. 1984. pp. 9-37.
Author Unknown. International Union of Biochemistry: Enzyme Nomenclature 1984. *Eur. J. Biochem.* vol. 152. 1985. p. 1.
Juszczyk et al. "Synthesis of orthogonally protected vicinal diamines with amino acid-based skeleton." *Letters in Peptide Science.* vol. 9. 2002. pp. 187-192.
Kokotos et al. "A Convenient One-Pot Conversion of N-Protrected Amino Acides and Peptides into Alcohols." *Synthesis.* 1990. pp. 299-301.
Mattingly. "Mono-Protected Diamines. $N^\alpha$ -tert-Butoxycarbonyl $\alpha,\omega$-Alkariediamine Hydrochlorieds from Amino alcohols." *Synthesis.* pp. 366-368, 1990.
Morris, Jr. et al. "Enterocci Resistant to Multiple Antimicrobial Agents, Including of Vancomycin: Establishment of Endemicity in A University Medical Center." *Annals of Internal Medicine.* vol. 123. No. 4. 1995. pp. 250-259.
O'Brien et al. "Inhibitors of Acyl-CoA:Cholesterol O-Acyl Transferase (ACAT) as Hypocholesterolic Agents. $8^1$ Incorporation of Amide or Amine Functionalites into a Series of Disubstituted Ureas and Carbamates. Effects on ACAT Inhibition in Vitro and Efficacy in Vivo." *J. Med. Chem.* vol. 37. 1994. pp. 1810-1822.
Bjorck et al. "Cystatin C, a Human Proteinase Inhibitor, Blocks Replication of Herpes Simplex Virus." *J. of Virology.* vol. 64. No. 2. 1990. pp. 941-943.
Stocka et al. "Inhibition of cruzipain, the major cysteine proteinase of the protozoan parasite, *Trypanosoma cruzi*, by proteinase inhibitors of the bystatin superfamily." *FEBS Letters.* vol. 370. 1995. pp. 101-104.

\* cited by examiner

*Primary Examiner*—Cecilia Tsang
*Assistant Examiner*—Christina Bradley
(74) *Attorney, Agent, or Firm*—Merchant & Gould P.C.

(57) ABSTRACT

The invention relates to compositions comprising a compound based on the general formula (I)

$$R_1\text{-Arg-}R_2\text{—NH—CH}(R_3)\text{—CH}_2\text{—NH—}R_4 \qquad (I)$$

and a carrier, diluent or an excipient.

6 Claims, 11 Drawing Sheets

ANTIMICROBIAL COMPOUNDS

FIELD OF INVENTION

The invention relates to compositions comprising a compound based on the general formula (I)

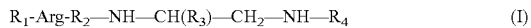

The composition may be used to eliminate and/or reduce microorganisms such as bacteria, viruses, fungi and protozoa.

BACKGROUND OF INVENTION

In the late 70ies, it was believed that bacterial diseases were satisfactorily controlled by antibiotics and, as well, future vaccines. Meanwhile, the appearance of new bacterial disease manifestations, such as *staphylococcal* and *streptococcal* toxic shock syndrome, the haemolytic-uremic syndrome and others, and rapidly increasing drug resistance worldwide have acted to challenge the view that bacterial diseases were largely defeated.

Antibiotic research at the industrial level was focused on the identification of more refined variants of already existing drugs—and newer penicillins, cephalosporins, macrolides and fluoroquinolones were marketed. However, only one antibiotic based on a novel antimicrobial principle, linezolide, was created during three decades—and resistance to the drug has already emerged during a few years of clinical use. Many antimicrobial peptides with new mechanisms of action have been reported; out of those active against bacteria most target the bacterial cell membrane by forming pores, for example antibiotics which are of microbial origin, and defensins, a large class of substances of mammalian origin. However, so far none of these substances has been developed into clinical use. Also, recent technical progress with combinatorial library technology has enabled the rapid design and testing of many substances intended for a defined target; again, in spite of considerable efforts no such compounds for medical use have been approved to date.

Resistance to old and newer antibiotics among bacterial pathogens is evolving rapidly, as exemplified by extended spectrum beta-lactamase (ESBL) and quinolone resistant gram-negatives, multi-resistant gonococci, methicillin resistant *Staphylococcus aureus* (MRSA), vancomycin resistant *enterococci* (VRE), penicillin non-susceptible *pneumococci* (PNSP) and macrolide resistant *pneumococci* and *streptococci* (Panlilo et al., Infect Control Hosp Epidemiol 1992;13: 582.586; Morris et al., Ann Intern Med 1995;123:250-259). An overuse, or improper use, of antibiotics is probably of great importance for triggering and spread of bacterial resistance.

Economically, drug resistant pathogens represent a major burden for health-care systems. For example, postoperative and other nosocomial infections will prolong the need for hospital care and increase antibiotic drug expenses. At the community level, the current situation with PNSP has highlighted, that most existing antibiotics may fail against this pathogen, earlier known to be invariably susceptible to antibiotics.

In the case of viral diseases, few drugs for treatment are available in spite of intense research. For HIV, the situation has improved by the combined use of some drugs with different targets, delaying progression of the disease. Regarding herpes viruses, there is a need for improved drugs for both systemic and localised manifestations. Also for the SARS virus, effective treatment alternatives are lacking.

SUMMARY OF THE INVENTION

The invention relates to a composition, such as a pharmaceutical and/or cosmetic composition being useful to combat microorganisms, such as bacteria, virus, fungi and protozoa as well as manufacturing of a medicament to be used to treat infections and/or disease caused by such microorganisms. Furthermore, the compound is effective to be used to reduce and/or eliminate combined infections, e.g. caused by both virus and bacteria or a mixture of bacteria.

According to one aspect, the invention relates to a composition comprising a) a compound having the following formula (I)

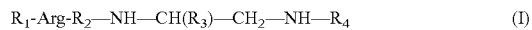

wherein $R_1$ is benzyloxycarbonyl or 3-phenylpropionyl, and $R_2$ is an amino acid residue selected from the group consisting of Leu, Ile, Val, Gly, Phe and Thr, and $R_3$ is selected from the group consisting of hydrogen, isopropyl, isobutyl, sec-butyl, 1-hydroxyethyl, benzyl, 4-hydroxybenzyl, phenyl and a 1,3 propylene bridge, additionally bonded to the nitrogen atoms of the diamine moiety as drawn

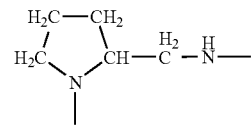

and $R_4$ is an acyl residue comprising a phenyl ring and b) a carrier, diluent or an excipient.

The composition being effective against various infectious diseases of viral, fungal, protozoan and bacterial origin.

According to another aspect, the invention relates to the use of said compound for the preparation of a medicament for the treatment of an infection and/or disease caused by a single or more than one microorganism.

According to still another aspect, the invention relates to a method of treating infections by administration of an effective amount of the composition.

By the use of solely one composition it is possible to reduce and/or eliminate more than one microorganism by the use of one and the same composition. However, the composition may also be used to combat one single microorganism. Since the compound shows effect against a broad spectrum of microorganisms its mechanism of action may be on a basic level implying low probability for microorganisms to develop resistance. We may also conclude from extensive testing that the action most probably differs from those of present antibiotics in clinical use.

BRIEF DESCRIPTION OF THE DRAWINGS

Further objects, features and advantages of the invention will appear from the following detailed description of the invention, reference being made to the accompanying drawings, in which.

DETAILED DESCRIPTION OF THE INVENTION

Definitions

Figure 1:
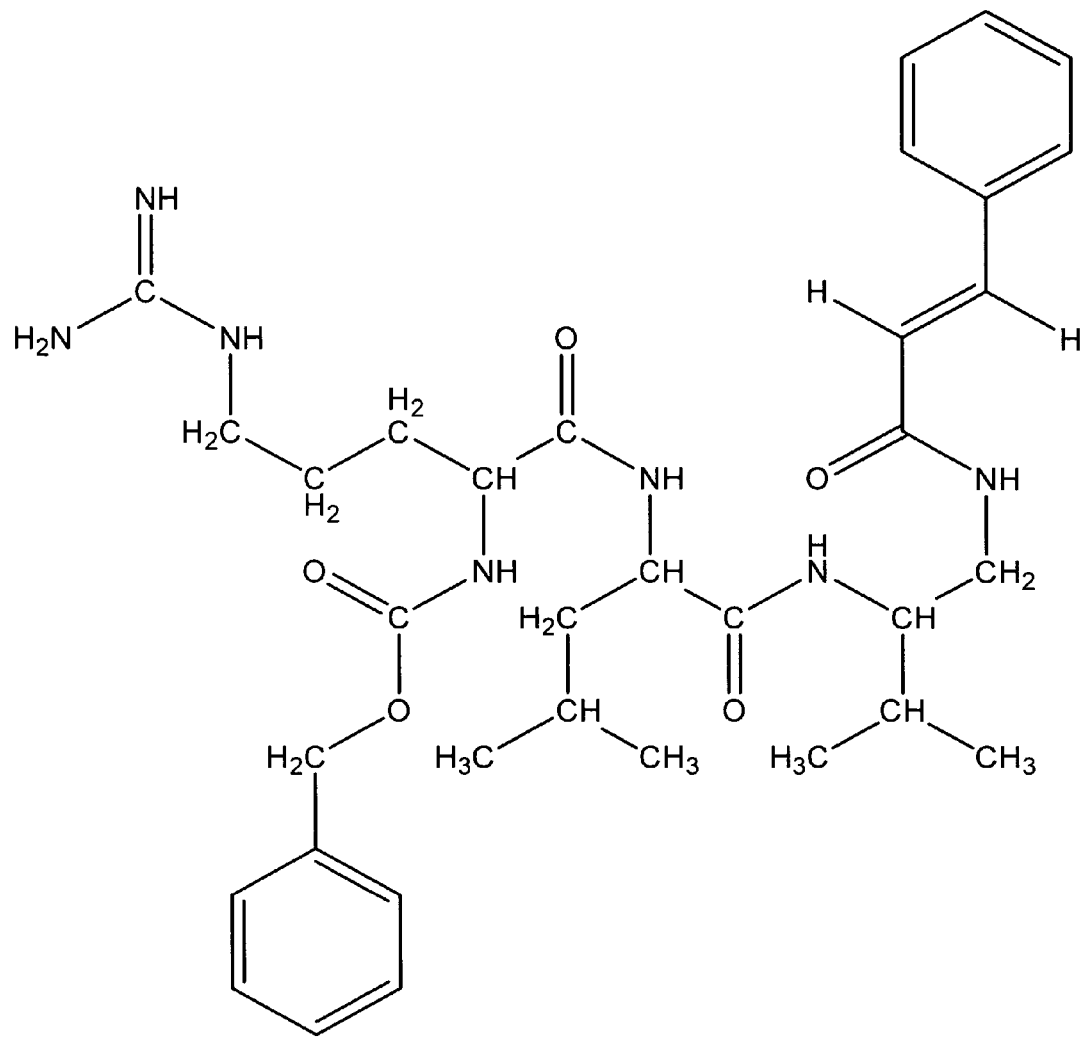
FIG. 1 illustrates one compound named Cp1 (cystapep 1).
Figure 2:
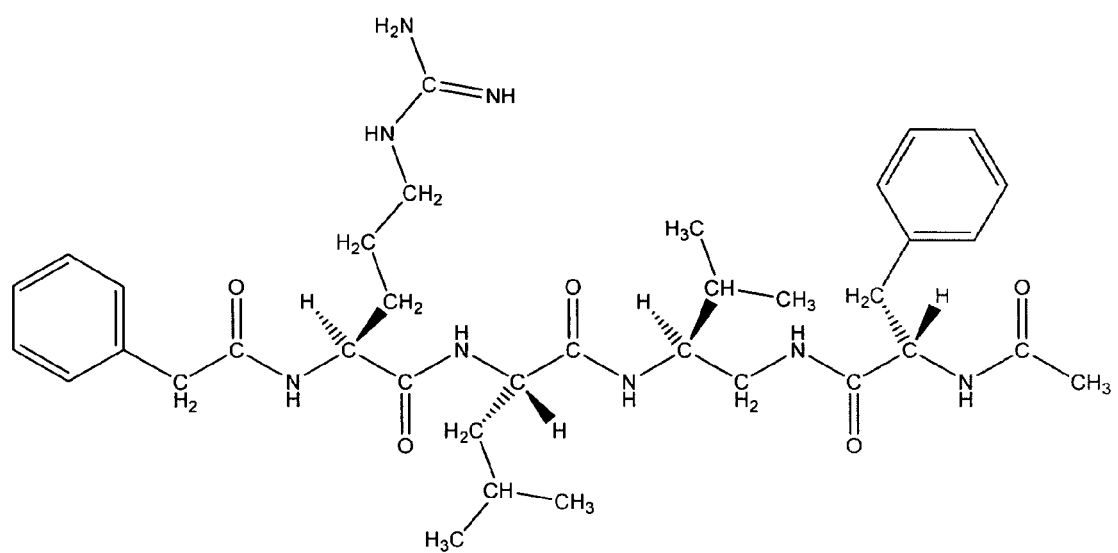
FIG. 2 illustrates another compound named (AcPhe⁵)Cp1 (cystapep 2).
Figure 3:
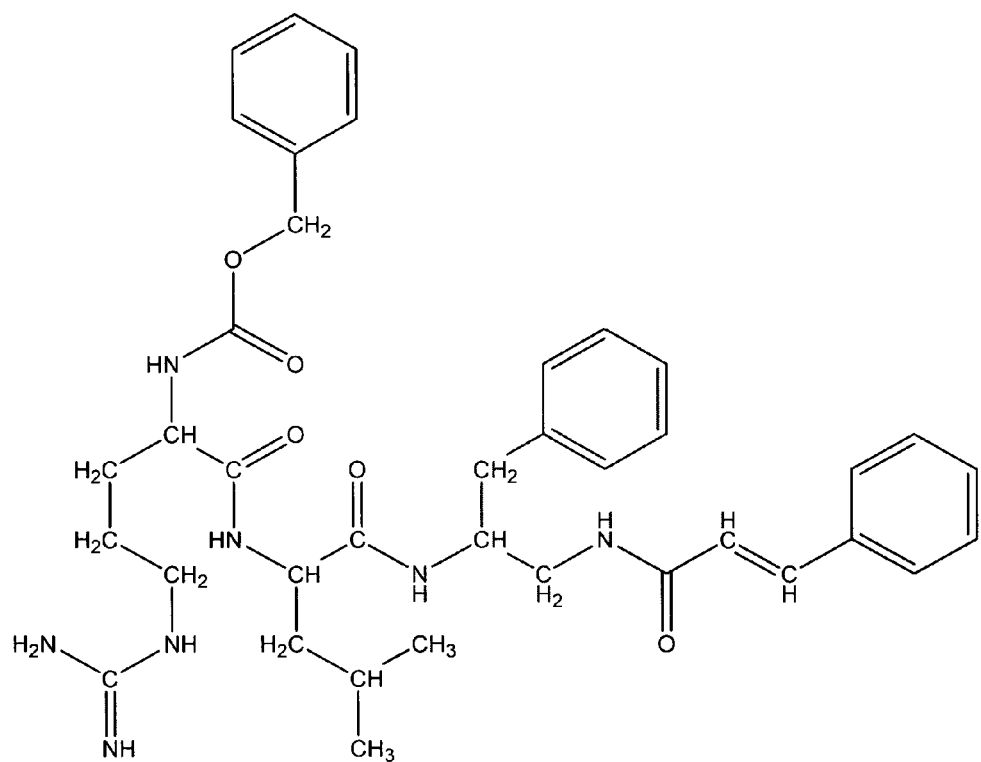
FIG. 3 illustrates a further compound named (Phe⁴)Cp1 (cystapep F).
Figure 4:
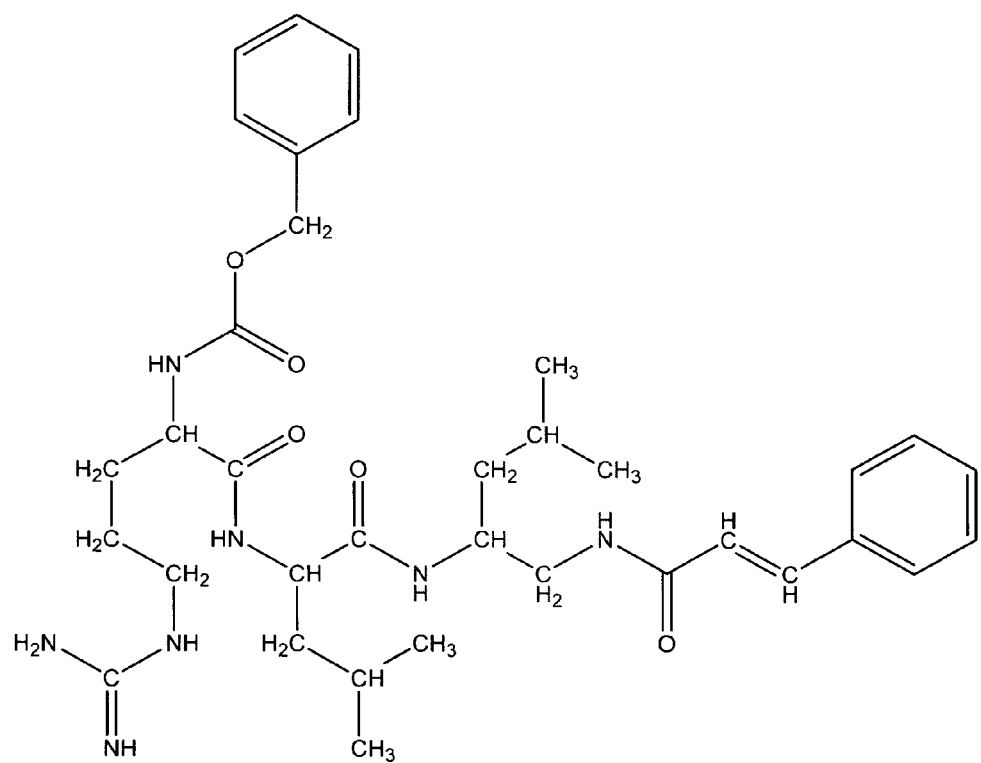
FIG. 4 illustrates a further compound named (Leu⁴)Cp1 (cystapep L).
Figure 5:
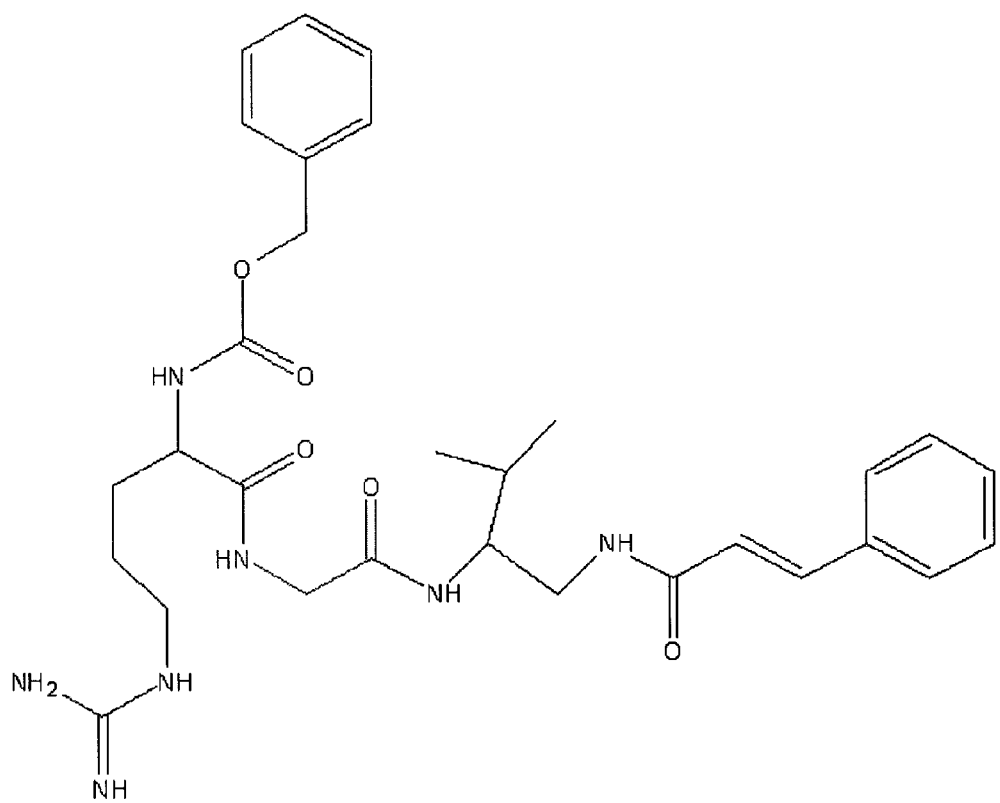
FIG. 5 illustrates a further compound named (Gly³)Cp1 (cystapep Gly 2).
Figure 6:
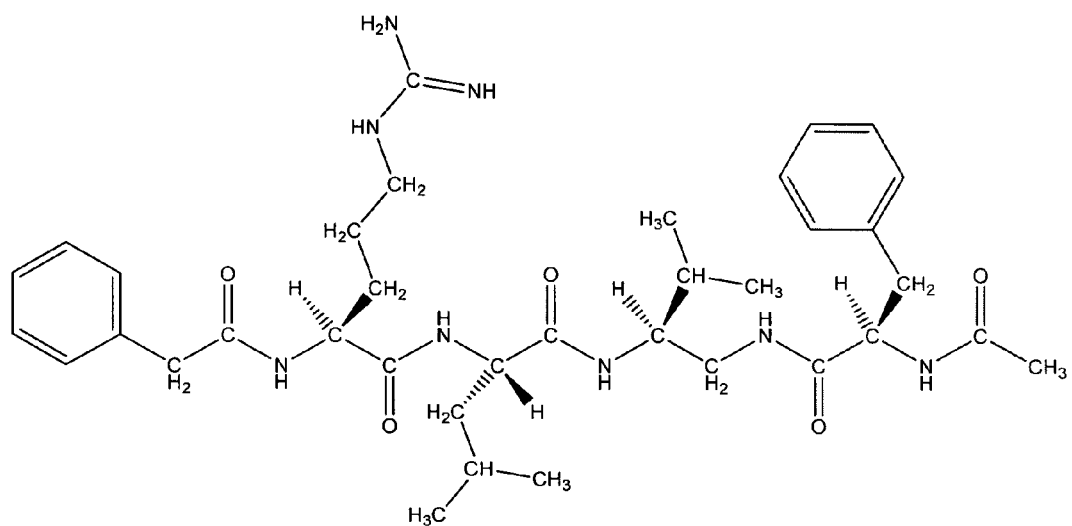
FIG. 6 illustrates a further compound named (Ac-D-Phe⁵) Cp1 (cystapep 2a).
Figure 7:
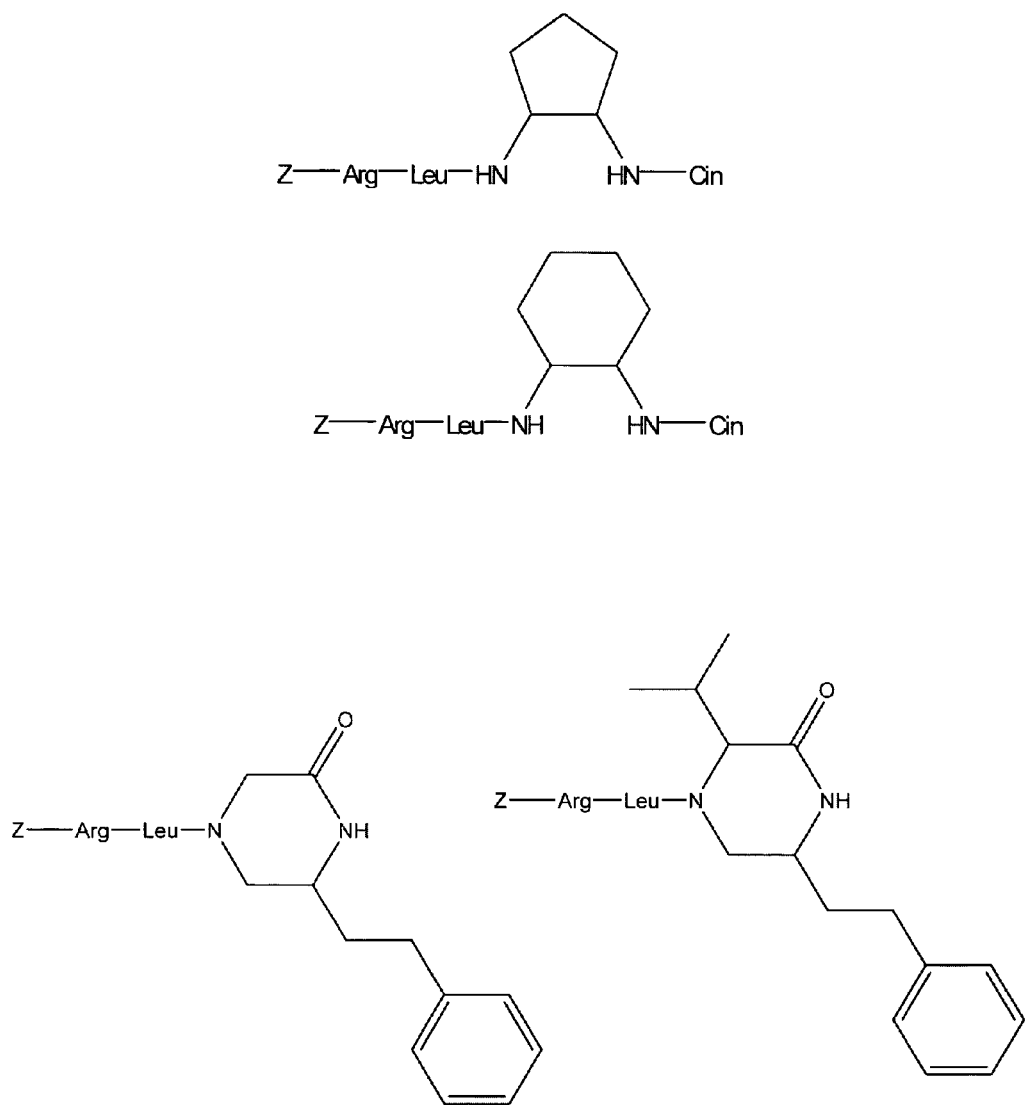
FIG. 7 illustrates further compounds.
Figure 8:
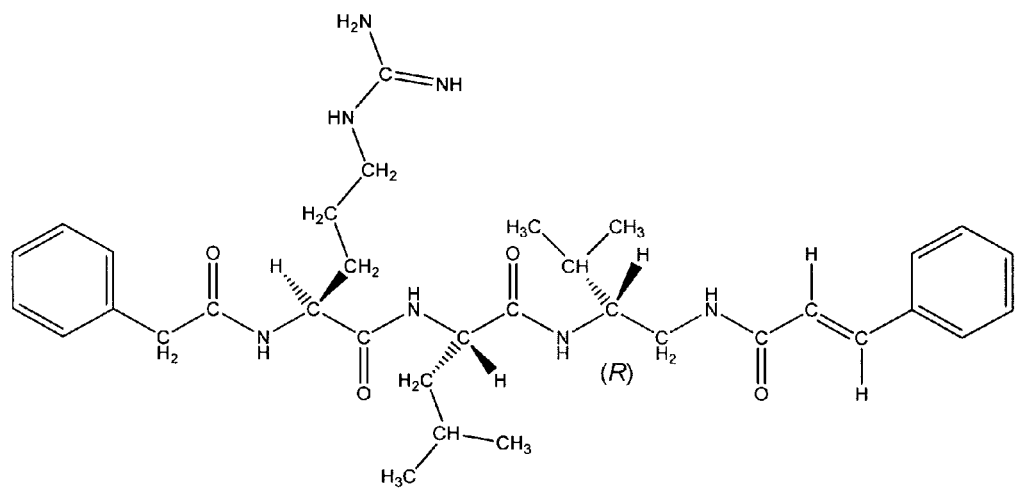
FIG. 8 illustrates a further compound named D-Val⁴Cp1
Figure 9:
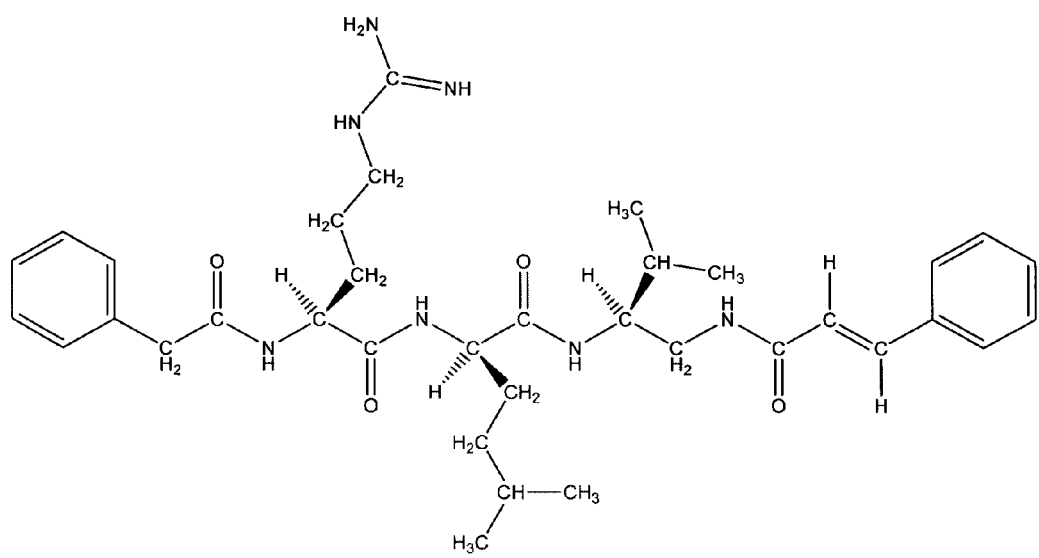
FIG. 9 illustrates a further compound named D-Leu³Cp1
Figure 10:
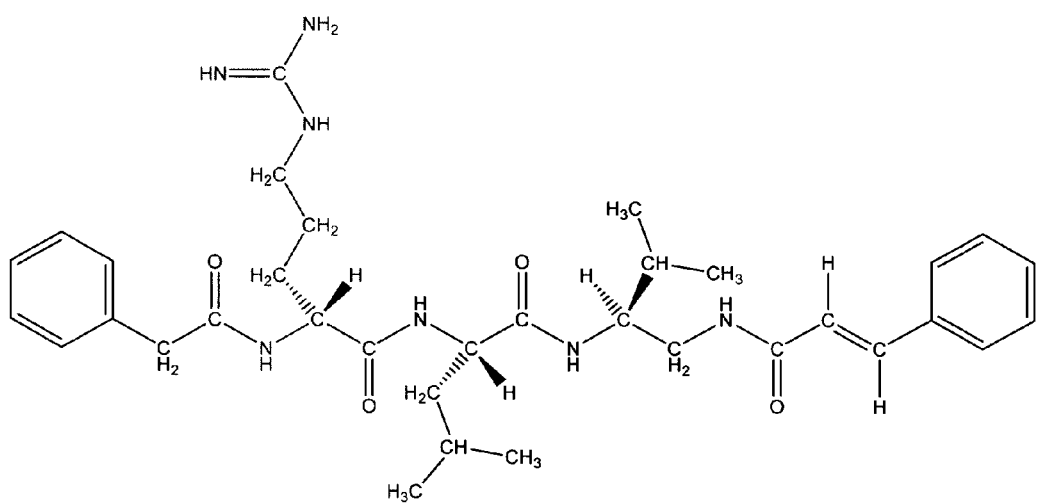
FIG. 10 illustrates a further compound named D-Arg²Cp1

In the context of the present application and invention the following definitions apply:

The term "resistant" is intended to mean resistant against at least one antimicrobial agent.

The term "multiresistant" is intended to mean at least resistant against two or more antimicrobial agents.

The term "compound"/"antimicrobial peptide" is intended to mean a compound/peptide which eliminates or inhibits the growth of bacteria, viruses, protozoans and/or fungi. The words "compound" and "peptide" are synonymously used within this particular application.

In the present context, amino acid names and atom names are used as defined by the Protein Data Bank (PDB) (www.pdb.org), which is based on the IUPAC nomenclature (IUPAC Nomenclature and Symbolism for Amino Acids and Peptides (residue names, atom names etc.), Eur J Biochem., 138, 9-37 (1984) together with their corrections in Eur J Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), phenylglycine (Phg), glutamine (Gln or Q), arginine (Arg or R), serine (Ser or S), threonine (Thr or T), valine (Val or V), tryptophan (Trp or W) and tyrosine (Tyr or Y), or derivatives thereof.

Composition

The invention relates to a composition comprising a) a compound having the following formula (I)

$$R_1\text{-Arg-}R_2\text{—NH—CH}(R_3)\text{—CH}_2\text{—NH—}R_4 \quad (I)$$

wherein $R_1$ is benzyloxycarbonyl or 3-phenylpropionyl, and $R_2$ is an amino acid residue selected from the group consisting of Leu, Ile, Val, Gly, Phe and Thr, and $R_3$ is selected from the group consisting of hydrogen, isopropyl, isobutyl, sec-butyl, 1-hydroxyethyl, benzyl, 4-hydroxybenzyl and phenyl and a 1,3 propylene bridge, additionally bonded to the nitrogen atoms of the diamine moiety as drawn:

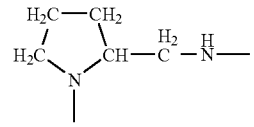

and $R_4$ is an acyl residue comprising a phenyl ring and b) a carrier, diluent or an excipient.

The above, identified compound, may be modified in a way such that the Arg group comprises an elongation or shortening of the Arg side chain without influencing the unique properties of the compound as a compound.

Additionally all kind of modifications may be introduced as long as the above defined general structure is maintained.

Accordingly, the fragment of the molecule comprising the diamine and $R_4$ residues may be replaced by the moiety derived from the group consisting of 6-phenetylpiperazin-2-one and 3-isopropyl-6-phenetylpiperazin-2-one. The chiral residues, i.e., the amino acid residues within the compound may be in the D or L-form without influencing the activity of the compound. The same applies for diastereomeric as well as enantiomeric forms.

Additionally, $R_4$ may be selected from the group consisting of cinnamoyl and phenylalanine or acyl residues derived from cinnamic acid, acetyl-D-phenylalanine, acetyl-L-phenylalanine and D or L-phenylalanine or derivatives thereof.

Said composition may be used to combat microorganisms, alone or in combinations. Example of bacteria are gram positive bacteria such as *Staphylococcus aureus*, coagulase negative *staphylococci* (CNS), β-haemolytic *streptococci* groups A, B, C and G (GAS, GBS, GCS and GGS), *pneumococci* and *Listeria* spp. Pathogenic viruses such as picorna virus in particular enterovirus, comprising poliovirus, coxsackieviruses groups A and B and Echoviruses and also Herpesviridae, in particular simplexvirus, comprising Herpes Simplex type 1 and 2. Other examples of viruses are hepatite A, B and C. Examples of fungus includes *Candida* ssp., in particular *C albicans*, dermatophytes and moulds The compound may be a cyclic compound wherein $R_1$ and $R_4$ are linked with Arg-Leu-Val or Orn-Leu-Val bridges.

Additionally, minor modification of the compound of the invention may be performed as long as the activity of the compound remains, such as modifications of the bonds between the residues derived from amino acids.

Specific examples of particularly interesting compounds are listed in the tables below.

| | Activity | |
|---|---|---|
| | Anti-bacterial | Anti-viral |
| $R_4$ | | |
| trans-cinnamoyl | + | + |
| Hydrogen— | + | |
| L-2-bromo-3-phenylpropionyl | + | |
| D-2-bromo-3-phenylpropionyl | + | |
| L-2-hydroxy-3-phenylpropionyl | + | |
| D-2-hydroxy-3-phenylpropionyl | + | |

-continued

| | Activity | |
|---|---|---|
| | Anti-bacterial | Anti-viral |
| (structure: phenyl-(CH$_2$)$n$-C(=O)-) | | |
| n = 1 | + | |
| n = 2 | + | |
| n = 3 – 7 | + | |
| trans-3-benzylacroyl | + | |
| (2S, 3S)-3-phenylglycidyl | + | |
| (2S, 3R)-3-phenylglycidyl | + | |
| (2S, 3S)-3-benzoylglycidyl | + | |
| trans-3-benzylsulphonylacroyl | + | |
| Phenylpropiolyl | + | |
| (E)-2-bromocinnamoyl | + | |
| Chloroacetyl | + | |
| 2-(4-pyridyl)acroyl | + | |
| Acetyl-L-phenylalanoyl | + | + |
| Acetyl-D-phenylalanoyl | + | + |
| 5-phenylpenta-2,4-dienoyl | + | |
| 4-phenylcinnamoyl | + | |
| $R_1$ = | | |
| Hydrogen— | + | |
| Acetyl | + | |
| Phenylacetyl | + | |
| 3-phenylpropionyl | + | |
| 4-phenylbutyryl | + | |
| Benzyloxtcarbonyl | + | |

| | Activity | |
|---|---|---|
| Compound | Anti-bacterial | Anti-viral |
| Z-Arg-Leu-Val-Phe-NH$_2$ | + | |
| Z-Arg-Leu-Val-cinnamoylamide | + | |
| Mpa-Phe-Arg-Leu-Val-Phe-Cys-NH$_2$ | + | |
| cyclo(Phe-Arg-Leu-Val-Phe-Arg-Leu-Val) | + | |
| cyclo(Phe-Arg-Leu-Val-Phe-Orn-Leu-Val) | + | |
| cyclo(Phe-Orn-Leu-Val-Phe-Orn-Leu-Val) | + | |
| cyclo(Phg-Arg-Leu-Val-Phg-Arg-Leu-Val) | + | |
| cyclo(D-Phg-Arg-Leu-Val-D-Phg-Arg-Leu-Val) | + | |
| cyclo(Tyr-Arg-Leu-Val-Tyr-Arg-Leu-Val) | + | |
| cyclo(D-Tyr-Arg-Leu-Val-D-Tyr-Arg-Leu-Val) | + | |

+ indicates that the compound show effects. Mpa-Phe indicates 3-phenylpropionyl

Examples are gram-positive bacteria, which may be combated by the invented compound and includes *S.aureus*, *S.epidermidis* and other coagulase negative *staphylococci* (CNS), *pneumococci*, groups A, B, C and G *streptococci*, and *Listeria monocytogenes*. Examples of viruses are polio and Herpes simplex, representing RNA and DNA viruses, respectively. Other examples are SARS, HIV, H5N1 as well as adeno-, coxsackie- and rhinoviruses. Examples of fungus are *Candia* spp, such as *C.grabrata, C. dermatophytes* as well as moulds.

For example one compound, named Cp1 (cystapep 1), is shown in FIG. 1. Cp1 reveals extensively modified amino acid residues, and lack of reactive sites; it is linear, amphipatic, soluble in DMSO to high concentrations but less soluble in water. It appears devoid of any detectable protease inhibitory activity. Since its small molecular size would enable transport through bacterial membrane pores, and it has low or no activity against gram-negative bacteria, its target of action may not be the cytoplasmatic membrane. Importantly, Cp1 shows a strong protective capacity for lethal *streptococcal* challenge in the mouse.

A large number of bacterial clinical isolates have been tested against Cp1 as well as against (AcPhe$^5$)Cp1, (Phe$^4$)Cp1, (Leu$^4$)Cp1, (Gly$^3$)Cp1 and (Ac-D-Phe$^5$)Cp1 (all shown in FIG. 1-6). Typical results are shown in the examples. Approximately 100 strains of MRSA (isolated at the University Hospital, Lund, Sweden), several with additional antibiotic resistance markers, were strongly inhibited in their growth—to a comparable level as antibiotic susceptible *S. aureus* strains, and no strains resistant to the above mentioned six compounds, or with impaired susceptibility, have been found. The same was true for antibiotic resistant *S.epidermidis* and group A *Streptococci* (GAS), as well as other β-haemolytic *Streptococci*, such as groups B, C and G strains, leading to the conclusion that the mode of action of the different compounds probably differs from that of most, or all, known antibiotics. Both GAS, *S.aureus* and *S.epidermidis* are known to produce cysteine proteases, but such enzymes in groups B, C and G *streptococci* and *pneumococci* as well as for *Listeria* have not been described; whether the defined compounds may still act through protease inhibition cannot be definitely ruled out at this point, in spite of evidence that it does not inhibit any of several cysteine proteases tested as mentioned above.

The in vitro antibacterial activity of drugs is commonly estimated by testing their minimal inhibitory (MIC) and bactericidal (MBC) concentrations. The MICs of Cp1 for both *S.aureus* and GAS were found to be approximately 16 mg/L, thus somewhat higher than for clinically effective drugs; however, these tests were performed in growth media without DMSO, implying solubility problems, and true MIC values might therefore be considerably lower. Furthermore, the finding that MIC and MBC were similar for tested species indicated that the antibacterial action of the defined compounds shown in the figures is bactericidal rather than bacteriostatic.

Experiments in cell culture have shown that the compounds shown in the figures are active against viruses, such as polio and Herpes simplex, representing RNA and DNA viruses, respectively. No cytopathic effects for the cell line used were recorded indicating that the compounds may not be toxic for eukaryotic cells. Additionally, the compounds may be used to combat other viruses such as SARS, HIV, H5N1, hepatite A,B and C and adeno-, coxsackie- or rhinoviruses, and fungi, i.e., *Candida* spp., such as *C. albicans*.

The compounds shown in the figures, are novel, short-chain peptidomimetics derivatives, structurally based upon the active site of human cystatin C. All display antibacterial activity against major human pathogens, such as *S.aureus*, CNS, groups A, B, C and G *streptococci*, and *L. monocytogenes*. They have low or no activity against gram-negative bacteria or α-haemolytic *Streptococci*. Such a property, from a clinical point of view, would be advantageous since most existing antibiotics exhibit harmful side-effects due to profound disturbances of the normal throat or gut flora. Notably, attempts in vitro to create bacterial mutants resistant to the compounds, have failed so far.

The difference between the different compounds shown in FIG. 1-6 are the following;

| Compound | Figure | $R_1$ | $R_2$ | $R_3$ | $R_4$ |
|---|---|---|---|---|---|
| Cp 1 | 1 | Benzyloxy-carbonyl | Leu | isopropyl | trans-cinnamoyl |

-continued

| Compound | Figure | R₁ | R₂ | R₃ | R₄ |
|---|---|---|---|---|---|
| [AcPhe⁵]Cp1 | 2 | Benzyloxy-carbonyl | Leu | isopropyl | N-Acetyl-phenylalanoyl |
| [Phe⁴]Cp1 | 3 | Benzyloxy-carbonyl | Leu | benzyl | trans-cinnamoyl |
| [Leu⁴]Cp1 | 4 | Benzyloxy-carbonyl | Leu | isobutyl | trans-cinnamoyl |
| [Gly³]Cp1 | 5 | Benzyloxy-carbonyl | Gly | isopropyl | trans-cinnamoyl |
| [Ac-D-Phe⁵]Cp1 | 6 | Benzyloxy-carbonyl | Leu | isopropyl | N-Acetyl-D-phenylalanoyl |

The compounds may be produced using conventional methods well known for a person skilled in the art. Possible methods can be found in the examples.

The above, mentioned compositions are suitable for medical use, and there are several kinds of human infection with current treatment problems that may potentially be treated/cured. Depending on the causative microbe(s) the compounds may be used alone or in combination with other antimicrobial agents to combat bacterial, viral, fungal and/or protozoan infection(-s).

Among bacterial diseases, systemic and local infections with MRSA (methicillin resistant *S.aureus*), with extensive resistance to antibiotics and increasing prevalence worldwide, may be the most important category. For the same reason, treatment of opportunistic infections caused by coagulase negative *streptococci* (CNS) often nosocomial and foreign device related, may be suitable for treatment with the above mentioned compounds, such as those shown in the figures. For pathogenic *streptococci*, antibiotic resistance is of current concern; however, invasive infections caused by *streptococci* are often life threatening in spite of antibiotic treatment, and successful treatment might require drugs with targets distinct from these of hitherto available antibacterial drugs. Additionally, common throat and skin infections caused by *streptococci*, often relapsing following antibiotic treatment, may be suitable for future treatment with the above, mentioned compounds.

The compounds according to the invention may also be used in the treatment of viral infections or diseases, such as oral, genital or systemic, caused by virus, such as herpes viruses.

"Pharmaceutically acceptable" means a diluent, buffer, carrier or excipient that at the dosage and concentrations employed does not cause any unwanted effects in patients. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The composition may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, gelatin, sodium alginate, polyvinyl-pyrrolidine, and/or polyvinyl alcohol, and tableted or encapsulated for conventional administration. Alternatively, the compounds may be dissolved in saline, water, polyethylene glycol, propylene glycol, ethanol, oils, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The compositions may be subjected to conventional pharmaceutical operations such as sterilisation and/or may contain conventional adjuvants such as preservatives, stabilisers, wetting agents, emulsifiers, buffers, fillers, etc., e.g. as disclosed elsewhere herein.

The composition according to the invention may be administered locally or systemically, such as topically, intravenously, orally, parenterally or as implants, and even rectal use is possible. Suitable solid or liquid pharmaceutical preparation forms are, for example, granules, powders, tablets, coated tablets, (micro)capsules, suppositories, syrups, emulsions, gels, ointments, suspensions, creams, aerosols, drops or injectable solutions in ampoule form and also preparations with protracted release of active compounds, in which preparations excipients, diluents, adjuvants or carriers are customarily used as described above. The composition may also be provided in bandages or plasters or the like.

The composition will be administered to a patient in a pharmaceutically effective dose. By "pharmaceutically effective dose" is meant a dose that is sufficient to produce the desired effects in relation to the condition for which it is administered. The exact dose is dependent on the activity of the compounds, manner of administration, nature and severity of the disorder, age and body weight of the patient and adjustment of dosage may thus be needed. The administration of the dose can be carried out both by single administration in the form of an individual dose unit or else several smaller dose units and also by multiple administrations of subdivided doses at specific intervals.

The composition according to the invention may be administered alone or in combination with other therapeutic agents, such as antibiotics or antiseptic agents. Examples are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, chlorhexidine, polyhexanide and other biguanides, acetic acid, and hydrogen peroxide. These agents may be incorporated as part of the same composition or may be administered separately.

The invention also relates to the use of the above defined compounds for the manufacture of medicaments for the treatment of an infections and/or diseases caused by one microorganism or a mixture of microorganisms as discussed above in connection with the above defined compositions.

Finally the invention relates to a method of treating a mammal, such as an animal or a human being having such an infection and/or disease.

Following examples are intended to illustrate, but not to limit, the invention in any manner, shape or form, either explicitly or implicitly.

EXAMPLES

Example 1

Figure 11:
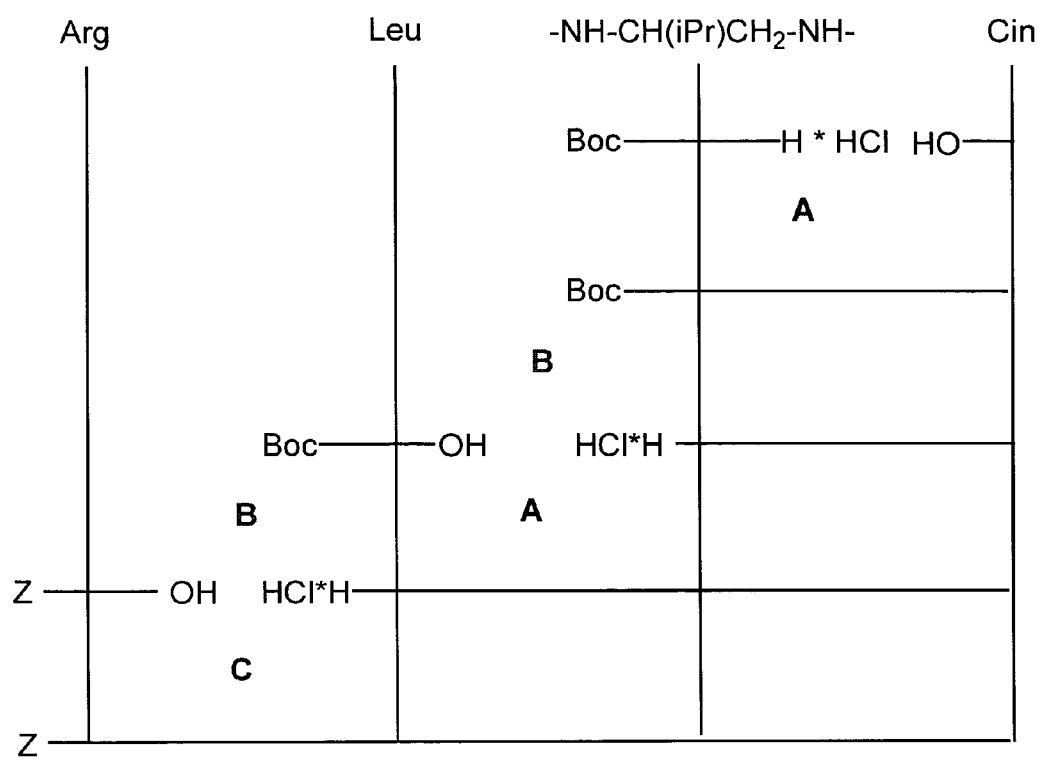
FIG. 11 shows an overview of the synthesis of the compounds.

Synthesis of the Different Compounds (General Scheme see FIG. 11)

Procedure A—Coupling.

10 mmol of the amine component (hydrochloride) was dissolved in 50 ml of dimethylformamide (DMF). Next, 1.4 ml (10 mmol) of triethylamine, 12 mmol of carboxy-component and 18 mmol of 1-hydroxybenzotraizole (HOBt) was added. The mixture was cooled on ice bath and 12 mmol of dicyclohexylcarcodiimide (DCC) was added in small portions during 30 min., with vigorous stirring. The reaction mixture was stirred on ice bath 1 hour, and then left at room temperature overnight. The precipitated dicycolhexylurea (DCU) was filtered off and washed with DMF, and the combined filtrates were evaporated to dryness under reduced pressure. The solid residue was dissolved in ethyl acetate, and the resulting solution was washed with water (1×100 ml), ice-cold 1N HCl (3×50 ml), water (1×ϕml) saturated NaHCO₃ (3×50 ml) and finally with water (3×70 ml). The organic layer was dried over anhydrous MgSO₄. The drying agent was filtered off, pre-washed with ethyl acetate and the combined filtrates were evaporated to dryness under reduced pressure. The solid residue was dissolved in hot toluene and precipitated with petroleum ether. Yield approximately 90%.

Procedure B—Deprotection.

The Boc-protected compound (10 mmol) was dissolved in 50 ml 4 N solution of (anhydrous) HCl in dioxane. The solution was stirred during 30 min. at room temperature, and then evaporated under reduced pressure to dryness. The solid residue was triturated with anhydrous diethyl ether. The solid residue was filtered off, washed with anhydrous diethyl ether and dried.

Procedure C—Coupling with Z-Arg-OH

The amino-component (10 mmol) was dissolved in DMF (70 ml), and 4.59 g (30 mmol monohydrate) HOBT was added. To the solution was diisopropyletylamine (DIPEA) added dropwise, until the pH of the mixture, controlled with wet indicator paper reached 7-8. Next, the N-benzyloxycarbonyl-arginine hydrochloride (5.17 g, 15 mmol) was added and the solution was cooled on ice bath. N,N'-Dicyclohexylcarbodiimide (3.09 g, 15 mmol) was added in small portions during 1 h. and after additional 1 h of stirring, the reaction mixture was left in a cold room overnight (approximately 4° C.). The precipitated DCU was filtered off and washed with a small volume of DMF and the combined filtrates were evaporated under reduced pressure. From the resulting mixture cystapep 1 (or its analogues) was isolated using chromatography techniques.

Isolation of Cystapep 1 or its Analogue, Hereinafter Only Named Cystapep 1

Small amounts (100-200 mg) of Cystapep 1 may be isolated using SPE technique on RP-C-18 stationary phase, or directly purified on RP-HPLC column (20×250 mm) filled with Kromasil-100-5-C8. The mobile phases contained triethylamine phosphate buffer (TEAP, pH=3, 0.05-0.2 M). Fractions containing Cystapep 1 were combined and the acetonitrile was removed by evaporation under reduced pressure. The resulting solution was pumped through the Kromasil column equilibrated with 5% MeCN-0.1% trifluoroacetic acid (TFA). The column buffer was washed out with 5% MeCN-0.1% TFA, next Cystapep 1 was eluted using a gradient of 5-50% MeCN containing 0.1% TFA during 1 hour. Fractions containing Cystapep 1 were concentrated and lyophilized. The substance obtained by this manner substance contains TFA as a counter ion.

Alternatively, a procedure was used that comprised isolation of Cystapep1 using SP-Sepharose FF, wherein large excess of the ion exchanger (100× molar excess or more) was used. The Sepharose column was equilibrated with 0.005 M sodium acetate-acetic acid buffer (pH=4.75) in 50% MeOH. The sample containing Cystapep1 was injected into the column and unbounded substances were eluted with 50% MeOH containing 0.005 M acetate buffer. Next, the Cystapep1 was eluted with a gradient of KCl (0-0.2 M). Due to weak solubility of Cystapep1 in the presence of salts, the resulting peak was very broad, especially when the injected amount of Cystapep1 was large. A narrower peak was obtained, when ammonium acetate was used in the place of potassium chloride. The fractions containing Cystapep1 were combined and evaporated to dryness. The Cystapep was extracted with anhydrous MeOH and purified by RP-HPLC. When ammonium acetate was used, the salt was removed by lyophilization.

The final purification of Cystapep 1 was performed using a Kromasil column, using approximately 29% MeCN-0.1M TEAP, pH=3 as a mobile phase or ca. 29% iPrOH-0.2 M ammonium acetate-acetic acid buffer (pH=5) as a mobile phase. In this last case, the additional desalting step is not necessary, because the ammonium acetate may be removed by lyophilization, Synthesis of Mono-Boc-Protected Diamines Desired Boc-protected alcohols may be obtained from proper Boc amino acid, in accordance with the literature procedures [1, 2]. Obtained Boc-aminoalcohols were converted into mono-Boc-protected diamines in accordance with literature procedures [3,4]. The best results were obtained when a combination of these two procedures was used. The mesyl-derivative of alcohol was obtained in accordance to the procedure of [4]. The azide was obtained generally in accordance with the same procedure, but in the presence of tetrabutylammonium bromide, like in the procedure of [3]. The inorganic salts were filtered off, washed with dimethylformamide and the combined filtrates were evaporated under reduced pressure. The oily residue was dissolved in diethyl ether and treated in this same manner as described in [3]. The reduction of azide to amine was carried out as described in [3]

In specific embodiments the mono-Boc-protected diamine is acylated with Z-Phe (D or L-isomer), next the Z (benzyloxycarbonyl) protective group is removed by hydrogenolysis, and the resulting compound is acetylated with acetic anhydride.

REFERENCES

1. Kokotos G. *A convenient one-pot conversion of N-protected amino acids and peptides into alcohols.* Synthesis 1990: 299-30.
2. Juszczyk P. Lankiewicz L. Kolodziejczyk A. *Synthesis of othogonally protected vicinal diamines with amino acid-based skeleton.* Lett. Pep.Sci. 2002;9:187-92
3. Mattingly P. G. *Mono-protected diamines. $N^\alpha$-tert-butoxycarbonyl-α,ω-alkanediaminehydrochlorides from amino alcohols.* Synthesis 1990: 366-8.
4. O'Brien P. M. Sliskovic D. R. Blankley J. Roth B. D. Wilsom M. W. Hamelehle K. L. Krause B. R. Stanfield R. L. *Inhibitors of acyl-Co-A transferase (A CAT) as hypocholesterolemic agents. Incorporation of amide or amine functionalities into a series of disubstituted ureas and carbamates. Effect of ACAT inhibition in vitro and efficacy in vivo.* J.Med. Chem. 1994;37:1810-22.

Example 2

Synthesis of Cp1 (Cystapep 1)

The (2S)-1-amino-2-tert-butyloxycarbonylamino-3-methylbutane hydrochloride was obtained from tert-butyloxycarbonyl-L-valine in accordance with the literature procedures [1, 2]. m.p. 175-176° C.; $[\alpha]_D^{22}$=+5| (c=1, ethanol).

Elemental analysis: calculated: 50.31% C, 9.71% H, 11.73% N; found: 49.65% C, 9.74% H, 11.76% N; IR (KBr): 3375 (NH, urethane), 2876 ($NH_3^+$, amine) 1683, (C=O urethane), 1165 (C—O, urethane) [$cm^{-1}$]

Synthesis of (2S)-2-Tert-Butyloxycarbonylamino-1-Trans-Cinnamoylamino-3-Methylbutane.

The solution of (2S)-1-amino-2-tert-bytyloxycarbonylamino-3-methylbutane hydrochloride (2.38 g 10 mmol), triethylamine (1.7 ml, 12 mmol), HOBt(2.70 g. 20 mmol) and trans-cinnamic acid (1.77 g, 12 mmol) in 50 ml of tetrahydrofurane (THF) was cooled in an ice bath, and DCC (1.54 g, 7.5 mmol) was added in small portions, during 30 min. The stirring was continued for 1 hour, and next the reaction mixture was left in room temperature overnight. The precipitate DCU was filtered off and washed with two portions of THF (15 ml of each).

Combined filtrates were evaporated under reduced pressure and the solid residue was dissolved in 150 ml of ethyl acetate. The solution obtained was washed with ice-cold 1M hydrochloric acid (3×50 ml), water (100 ml), a saturated water solution of sodium bicarbonate (3×50 ml) and saline (2×50 ml). The organic layer was dried over anhydrous magnesium sulphate and evaporated to dryness. The resulting solid was crystallized from toluene-petroleum ether, yielding 2.95 g (88.7%) of (2S)-2-tert-butyloxycarbonylamino-1-trans cinnamoylamino-3-methylbutane, m.p.=149-151° C.; $[\alpha]_D^{20}$=–0.9|° C. (c=1, methanol).

Elemental analysis: calculated: 68.65% C, 8.49% H, 8.49% N; found: 68.69% C, 8.73% H, 9.01% N. IR (KBr) 3359 (NH, urethane), 3326 (N—H, amide), 1688 (C=O, urethane), 1173 (C—O, urethane), 964 (=C—H, cinnamoyl), 764 (CH, phenyl), 723 (CH phenyl) [$cm^{-1}$].

Synthesis of (2S)-2-[(N$^\alpha$-Tert-Butyloxycarbonyl-Leucyl)-Amino]-1-Trans-Cinnamoylamino-3-Methylbutane.

(2S)-2-tert-Butyloxycarbonylamino-1-trans-cinnamoylamino-3-methylbutane (2.5 g. 7.5 mmol) was dissolved in 40 ml of 4N hydrochloride in anhydrous dioxane. The reaction mixture was stirred during 30 min. at room temperature and evaporated under reduced pressure. The residue was triturated with 50 ml of anhydrous diethyl ether, filtered under reduced pressure, washed twice with diethyl ether (2×20 ml) and dried in a vacuum desiccator over potassium hydroxide. The resulting (2S)-2-amino-1-cinnamoylamino-3-methylbutane hydrochloride (1.78 g, 7.35 mmol) was dissolved in 50 ml of THF and triethylamine (1 ml, 7.5 mmol), HOBt (2.00 g, 15 mmol) and Boc-L-leucine monohydrate (1.87 g, 7.5 mmol) were added to the solution. The mixture was cooled on ice bath and DCC (1.54 g, 7.5 mmol) was added in small portions, during 30 min., with vigorous stirring. The mixture was stirred in an ice bath for one additional h and left at room temperature overnight. The precipitated DCU was filtered off, washed with THF (2×15 ml) and the combined filtrates were evaporated under reduced pressure. The solid residue was dissolved in 100 ml of ethyl acetate and the solution was washed with ice-cold 1M hydrochloric acid (3×50 ml), water (100 ml), a saturated aqueous solution of sodium bicarbonate (3×50 ml) and saline (100 ml). The organic layer was dried over anhydrous magnesium sulphate and evaporated to dryness. The residue was dissolved in hot toluene and precipitated with petroleum ether, yielding 2.97 g (88.9%) of (2S)-2-[(N-tert-butyloxycarbonyl-leucyl)-amino]-1-trans-cinnamoylamino-3-methylbutane.

Synthesis of (2S)-2-[(N$^\alpha$-Benzyloxycarbonyl-Arginyl-Leucyl)-Amino]-1-Trans-Cinnamoylamino-3-Methylbutane (Cp 1).

(2S)-2-[(N-tert-Butyloxycarbonyl-leucyl)-amino]-1-trans-cinnamoylamino-3-methylbutane (0.668 g, 1.5 mmol) was dissolved in 25 ml of 4 N solution of anhydrous hydrochloride in dioxane. The reaction mixture was stirred during 30 min. at room temperature and then evaporated to dryness under reduced pressure. The residual oil was triturated with anhydrous diethyl ether (50 ml). The obtained solid was filtered off under reduced pressure, washed with anhydrous diethyl ether (3×20 ml) and dried under vacuum over potassium hydroxide. The resulted (2S)-2-(leucylamino)-1-(trans-cinnamoylamino)-3-methylbutane hydrochloride (0.545 g, 1.43 mmol) was dissolved in 10 ml of DMF. Next, HOBt, (0.405 g, 3 mmol) was added and pH of the mixture was adjusted to 7.5 with triethylamine (controlled with wet indicator paper), and then the N$^\alpha$-benzyloxycarbonyl-arginine hydrochloride (1.034 g, 3 mmol) was added. The reaction mixture was cooled on ice bath, and then the DCC (0.619 g, 3 mmol) of was added in small portions during 30 min. The mixture was stirred during additional 1 hour on ice bath and overnight at room temperature. The precipitated DCU was filtered off and washed with 20 ml of DMF. Combined filtrates were evaporated and the resulted residue was dissolved in 200 ml of 50% aqueous ethanol acidified with 20 ml of acetic acid. The solution was filtered and pumped through chromatographic column (50×200 mm) filled with S-Sepharose FF, equilibrated with 0.001 M sodium acetate-acetic acid buffer (pH=4.75) in 50% ethanol. The column was washed with an additional 750 ml of 0.001 M sodium acetate-acetic acid buffer in 50% ethanol, and the product was eluted with the linear gradient of potassium chloride (from 0 to 0.2 M of KCl in total amount of 2 l of eluent. Flow rate-20 ml/min). Fractions containing Cystapep 1 were collected, evaporated to dryness and extracted with 50 ml of methanol. The insoluble inorganic salts were filtered off, washed with 20 ml of methanol and combined filtrates evaporated to dryness. The residue (1.1 g) was dissolved in 30 ml of 29% (v/v) isopropanol-water solution containing 0.2 M of TEAP buffer (pH=2.8). Half of the solution was injected on the RP-HPLC column (50×250 mm, filled with Kromasil Kr-100-7-C-8), equilibrated with 29% (v/v) isopropanol-water solution containing 0.2 M of TEAP buffer and eluted with this same solvent system (isocratic elution), at flow rate 25 ml/min. The eluate was monitored using UV detector at λ=226 nm. Fractions containing pure Cystapep 1 were collected, evaporated to half of volume and pumped through the same column equilibrated with 0.1% TFA in 5% solution of isopropanol (iPrOH) in water (v/v/v) (5% iPrOH, 0.1% TFA/$H_2O$). The column was washed out with additional 1.5 l of 0.1% TFA in 5% solution of iPrOH in water, and next, the Cystapep 1 was eluted in gradient from 5% iPrOH, 0.1% TFA/$H_2O$ to 50% iPrOH, 0.1% TFA/$H_2O$ during 90 min. Flow rate 25 ml/min, monitoring of the eluate as described above. Fractions containing Cystapep 1 were collected, concentrated under reduced pressure and lyophilized. The second half of the crude Cystapep 1 solution was worked up in the same manner. Yield-0.682 g (60.6%) of Cystapep 1 as trifluoroacetate salt. =−16.9° (c=1, methanol);

MS (MALDI-TOF): m/z=636.4 [M+H]$^+$Elemental analysis: calculated (for $C_{34}H_{49}N_7O_5.TFA.H_2O$): 56.31% C, 6.83% H, 12.77% N; found: 56.70% C, 6.70% H, 12.45% N. IR (KBr) [cm$^{-1}$]: 3299 (NH), 1655 (C=O, urethane) 1642 (C=O amide), 1181 (C—O urethane), 766 (CH phenyl), 721 (CH phenyl)

DMSO was applied to each hole. After prediffusion at room temperature for 0.5 h the plates were incubated at 37° C. for 14 h aerobically or in 5% $CO_2$ atmosphere as described above.

MIC/MBC determinations were performed by broth dilution according to established procedures, well known for a person skilled in the art.

The results are summarised below.

| Bacterial strain | Cp 1 | [AcPhe$^5$]Cp1 | [Phe$^4$]Cp1 | [Leu$^4$]Cp1 | [Gly$^3$]Cp1 | [Ac-D-Phe$^5$]Cp1 |
|---|---|---|---|---|---|---|
| *Staphylococci* incl. multiresistant MRSA | + | + | + | + | + | + |
| CNS incl. resistant and multiresistant MRSE | + | + | + | + | + | + |
| *Streptococcus*: group B | + | + | + | + | + | + |
| *Streptococcus*: group C | + | + | + | + | + | + |
| *Streptococcus*: group G | + | + | + | + | n.d. | + |
| *Streptococcus*: group A | + | + | + | + | n.d. | + |
| *L. monocytogenes* | + | + | n.d. | n.d. | n.d. | + |
| *S. pneumoniae* | + | + | + | + | n.d. | n.d. |
| *E. coli* and other Gram-negatives | − | − | − | − | n.d. | n.d. |
| α-haemolytic *Streptococci* | − | − | − | − | − | − |

+ indicates antibacterial effect, − indicates no or low antibacterial effect and n.d., indicates not determined Test of Concentration of the Compounds Different solutions of the different Cystapeps shown in the figures were centrifuged at 300 g for 15 min. Aliquots of the clear supernatants were used for quantitative amino acid analysis after evaporation followed by hydrolysis at 110° C. for 20 h in 6M HCl. An automated system, Beckman High Performance Analyzer, model 6300, was used for the amino acid analysis. The amounts of amino acids released were then used to calculate the concentration of the different compounds from their known structures.

Example 3

Antibacterial Analysis

Clinical isolates and reference strains including *Streptococcus pyrogenes* type M1, *Streptococcus agalactiae* (NCTC 8181), *Streptococcus equisimilis* (ATCC 12388), *Streptococcus pneumoniae* (ATCC49619), *Staphylococcus aureus* (ATCC 29213), *Staphylococcus epidermidis* (ATCC 14990) were tested. The clinical isolates were isolated by the University Hospital, Lund, Sweden and included a variable numbers of *S.aureus* including MRSA, CNS, groups A, B, C and G streptococci (GAS; GBS; GCS; GGS, respectively), *Staphylococcus aureus*, coagulase negative *staphylococci* (CNS), *Enterococcus faecium*, viridans *streptococci*, *Streptococcus pneumoniae*, *Listeria monocytogenes*, *Moraxella catarrhalis*, *Haemophilis influenaae*, *E. coli*, *Klebsiella pneumoniae* and *Pseudomonas aeruginosa*.

The antibacterial activity of the different compounds was tested by agar well diffusion. Strains were grown aerobically at 37° C. for 18 hours on blood agar base (LabM) with 4% defibrinated horse blood. However, *Haemophilus influenzae* was grown on Blood agar base No 2 (Oxoid) containing 7% haematized horse blood in 5% $CO_2$ atmosphere. From each strain 5-10 colonies were suspended in 10 ml saline to an optical density of approximately 0.5 McFarlands units, vortexed rigorously and inoculated onto IsoSentitest agar (Oxoid), or onto haematin agar as indicated above, using cotton-tipped swab. The thickness of the solid media was 5 mm. Wells of 5 mm diameter were punched in the agar and 40 ul of a solution of each of the tested compounds (1 mg/ml) in Example 4

Antiviral Analysis Test substance; Acyclovir 1.0 mM Cystapep 1 (Cp1) 0.4 mM in 1% DMSO DMSO 1%

Inhibition Analysis

GMK (Green Monkey Kidney) AH 1 cells were grown in 24 well plates with 1 ml Minimum Essential Medium (MEM) cell culture medium containing glutamax (MEM-glutamax), 10% fetal calf serum and gentamicin (final conc 50 mg/L). When cells had reached a concentration of $5×10^5$ cells/well, the cell culture medium was removed and the cells incubated with HSV-1 F (Herpes Simplex Virus) (Ejercito et al., J Gen Virol 1968; 2:357-364) at a concentration of 10 PFU (plaque forming units)/cell or with poliovirus type 1 at a concentration of 1 PFU/cell. After 2 hours of incubation at 37° C. the virus containing medium was removed and the cells washed 4 times in PBS. Then 0.5 ml MEM-glutamax containing gentamicin (as above, conc 50 mg/L) with or without test substance was added. The cells were incubated for 48 hours at 37° C. in a $CO_2$ incubator and then frozen at −30° C.

Plaque Counting Test

Cell culture medium with the frozen cells obtained from the inhibition test was thawn and diluted in 7 steps from 1 to $10^{-7}$. The plaque titration was performed using GMK AH 1 cells in MEM-glutamax with gentamicin. The cells were washed three times with PBS and incubated in petri plates with different dilutions of the virus containing cell culture medium obtained in the inhibition test. The cells were incubated for 1 hour at 37° C. The medium was removed by washing the cells once with PBS. Then an agar (Bacto-Agar) overlay was added and the plates were incubated at 37° C. for 3 days. The plaques were counted (Johansson et al., Intervirology 1988; 29:334-338).

| Substance | HSV-1 plaques | Polio plaques |
|---|---|---|
| Medium | $3.8 × 10^8$ | $3.8 × 10^7$ |
| 1% DMSO | $3.9 × 10^8$ | $3.5 × 10^7$ |
| Cystapep 1 (Cp1) | $1.0 × 10^3$ | $2.6 × 10^5$ |
| Acyclovir | $2.4 × 10^3$ | n.a. | n.a.: not applicable (Leu⁴)Cp1 0.4 mM in 1% DMSO and (Phe⁴)Cp1 0.4 mM in 1% DMSO were analysed in the same way as Cystapep 1 and found to have effect against both HSV-1 and polio.

Example 5

Antifungal Activity

The minimal inhibitory concentration (MIC) was determined using a method with Sabouraud broth (Becton Dickinson) and an initial inoculum $10^3$-$10^4$ cfu/ml. Polypropylene 96-well plates (Nunc) were incubated at 25° C. for 48 h (for *Candida albicans* ATCC 10231) or 7 days (for *Aspergillus niger* ATCC 16404). The MIC was taken as the lowest drug concentration at which noticeable growth was inhibited. The experiments were performed in duplicate.

| Compound | MIC (□g/ml) *Candida albicans* ATCC 10231 | *Aspergillus niger* ATCC 16404 |
|---|---|---|
| Cp1 | 32 | 64 |
| (AcPhe⁵)Cp1 | 512 | 256 |

Example 6

Cp1 was added to a softening cream and 0.2 ml solution (0.1 g/l) was applied to an area of a beginning labial herpes outbreak on the lip of a female. After 3-4 hours the symptoms was gone. The experiment was performed twice.

The invention claimed is:

1. A composition comprising
a) a compound selected from the group consisting of

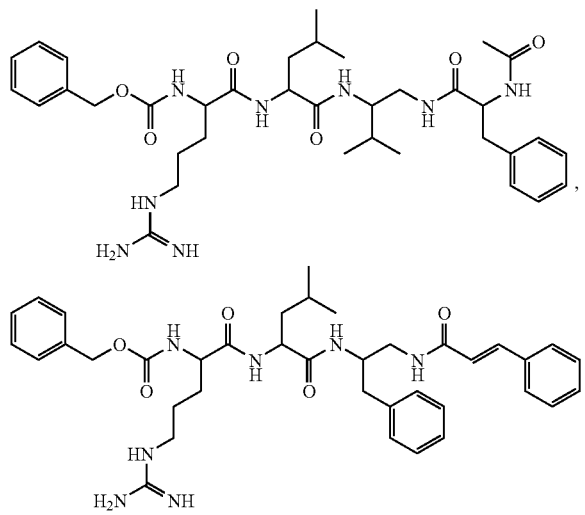

-continued

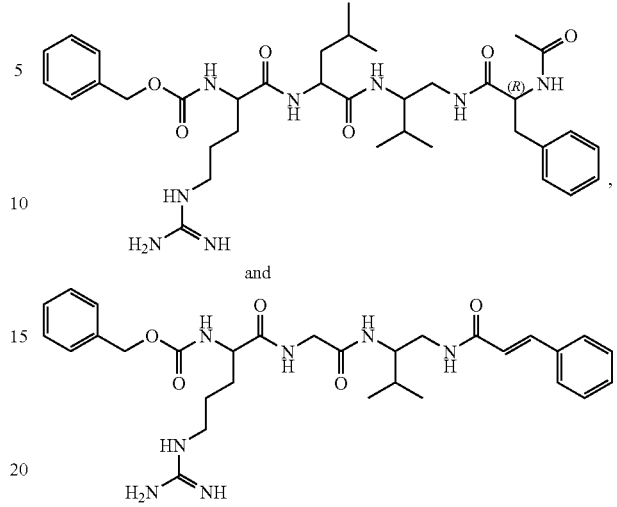

and b) a carrier, diluent or an excipient; wherein the composition is effective against a disease or a mixture of diseases caused by microorganisms selected from the group consisting of *Staphylococci, Pneumococci, Streptococci, Listeria, Candida* and *Aspergillus*.

2. The composition according to claim 1, wherein the *Staphylococci, Pneumococci, Streptococci* or *Listeria* comprises a resistant or multiresistant bacteria.

3. The composition according to claim 1, further comprising one or more therapeutic agents.

4. The composition according to claim 3, wherein the therapeutic agents are selected from the group consisting of penicillins, cephalosporins, carbacephems, cephamycins, carbapenems, monobactams, aminoglycosides, glycopeptides, quinolones, tetracyclines, macrolides, fluoroquinolones, antiseptic agents, biguanides, docosanol, acetic acid, and hydrogen peroxide.

5. The composition according to claim 1, wherein the composition is in the form selected from the group consisting of granules, powders, tablets, coated tablets, (micro) capsules, suppositories, syrups, emulsions, gels, ointments, suspensions, creams, aerosols, injectable solutions in ampule form, and drops.

6. A method of treating a mammal having a microbial infection or disease comprising administration of an effective amount of the composition according to claim 1, wherein said microbial infection or disease is caused by microorganisms selected from the group consisting of *Staphylococci, Pneumococci, Streptococci, Listeria, Candida* and *Aspergillus*.

* * * * *